US012577695B2

(12) United States Patent
Lee et al.

(10) Patent No.: US 12,577,695 B2
(45) Date of Patent: Mar. 17, 2026

(54) SYSTEM OF UTILIZING CARBON DIOXIDE

(71) Applicant: KOREA INSTITUTE OF SCIENCE AND TECHNOLOGY, Seoul (KR)

(72) Inventors: Ung Lee, Seoul (KR); Da Hye Won, Seoul (KR); Jai Hyun Koh, Seoul (KR); Dong Ki Lee, Seoul (KR); Hyung Suk Oh, Seoul (KR); Byoung Koun Min, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 721 days.

(21) Appl. No.: 17/724,609

(22) Filed: Apr. 20, 2022

(65) Prior Publication Data

US 2023/0057916 A1 Feb. 23, 2023

(30) Foreign Application Priority Data

Aug. 19, 2021 (KR) ........................ 10-2021-0109535

(51) Int. Cl.

*C25B 15/08* (2006.01)
*B01D 53/62* (2006.01)
*B01D 53/78* (2006.01)
*B01D 53/96* (2006.01)
*B01J 19/24* (2006.01)

(Continued)

(52) U.S. Cl.

CPC ............ *C25B 15/081* (2021.01); *B01D 53/62* (2013.01); *B01D 53/78* (2013.01); *B01D 53/965* (2013.01);

(Continued)

(58) Field of Classification Search

CPC ................................ C25B 1/23; C25B 15/081

See application file for complete search history.

(56) References Cited

U.S. PATENT DOCUMENTS 4,017,271 A * 4/1977 Barclay ...................... C10J 3/84
518/703

FOREIGN PATENT DOCUMENTS

EP 2096158 A1 * 9/2009 ............... C10G 2/32
JP 2005132739 A 5/2005

(Continued)

OTHER PUBLICATIONS

Machine translation of JP 2018-154900 A (Year: 2018).*

(Continued)

*Primary Examiner* — Harry D Wilkins, III

(74) *Attorney, Agent, or Firm* — Harness, Dickey & Pierce, P.L.C.

(57) ABSTRACT

A system of utilizing carbon dioxide comprises a carbon dioxide capturing device for capturing carbon dioxide, an electrochemical reaction device for producing synthetic gas by reducing the carbon dioxide captured by the carbon dioxide capturing device, a hydrogen carrier manufacturing device for manufacturing a hydrogen carrier material by using the synthetic gas produced by the electrochemical reaction device, a dehydrogenation device for producing hydrogen from the hydrogen carrier material manufactured by the hydrogen carrier manufacturing device, and a hydrogen utilization device for utilizing hydrogen produced by the dehydrogenation device, wherein the dehydrogenation device further produces carbon dioxide from the hydrogen carrier material and supplies the carbon dioxide to the carbon dioxide capturing device.

11 Claims, 5 Drawing Sheets

(51) Int. Cl.

| | |
|---|---|
| ***C07C 29/151*** | (2006.01) |
| ***C25B 1/23*** | (2021.01) |
| ***C25B 9/19*** | (2021.01) |
| ***C25B 9/70*** | (2021.01) |
| ***C25B 11/052*** | (2021.01) |
| ***C25B 11/065*** | (2021.01) |
| ***C25B 11/081*** | (2021.01) |
| ***H01M 8/0612*** | (2016.01) |
| ***H01M 8/0656*** | (2016.01) |

(52) U.S. Cl.

CPC ......... *B01J 19/245* (2013.01); *C07C 29/1518* (2013.01); *C25B 1/23* (2021.01); *C25B 9/19* (2021.01); *C25B 9/70* (2021.01); *C25B 11/052* (2021.01); *C25B 11/065* (2021.01); *C25B 11/081* (2021.01); *C25B 15/087* (2021.01); *H01M 8/0618* (2013.01); *H01M 8/0656* (2013.01); *B01D 2252/20431* (2013.01); *B01D 2257/504* (2013.01)

(56) References Cited

FOREIGN PATENT DOCUMENTS

| | | | | | |
|---|---|---|---|---|---|
| JP | 2017150072 A | | 8/2017 | | |
| JP | 2018154900 A | * | 10/2018 | ............... | C25B 1/00 |
| KR | 1020160036881 A | * | 4/2016 | ............. | C25B 15/08 |
| WO | WO-2012011252 A1 | | 1/2012 | | |
| WO | WO-2019204938 A1 | * | 10/2019 | ......... | B01D 53/1475 |

OTHER PUBLICATIONS

Machine translation of KR 20160036881 A (Year: 2016).*

Sasikumar et al, Aqueous methanol eletrolysis using proton conducting membrane for hydrogen production, International Journal of Hydrogen Energy, vol. 33, No. 21, Nov. 2008, pp. 5905-5910 (Year: 2008).*

Nursanto et al, Gold catalyst reactivity for CO2 electro-reduction: From nano particle to layer, Catalysis Today, vol. 260 , Feb. 2016, pp. 107-111 (Year: 2016).*

Translation of Office Action from Corresponding Korean Application No. 10-2021-0199535, Dated Aug. 4, 2023 (Year: 2023).*

Garbardo et al, Combined high alkalinity and pressurization enable efficient CO2 electroreduction to CO, Energy & Environmental Science, vol. 11, No. 9, Jun. 2018, pp. 2531-2539 (Year: 2018).*

Goeppert et al, Recycling of carbon dioxide to methanol and derived products—closing the loop, Chemical Society Reviews, vol. 43 , No. 23, Jun. 2014, pp. 7995-8048 (Year: 2014).*

Lee, W. H., et al.; "Highly selective and scalable CO2 to CO—Electrolysis using coral-nanostructured Ag catalysts in zero-gap configuration", Nano Energy 76 (2020) 105030, pp. 1-9.

* cited by examiner

SYSTEM OF UTILIZING CARBON DIOXIDE

CROSS-REFERENCE TO RELATED APPLICATIONS

This application claims the benefit of the Korean Patent Application No. 10-2021-0109535 filed on Aug. 19, 2021, which are hereby incorporated by reference as if fully set forth herein.

FIELD

The present disclosure relates to a system of utilizing carbon dioxide.

BACKGROUND

Balance in carbon circulation on the earth has been broken due to the increase of carbon dioxide in the atmosphere. A main reason in the increase of carbon dioxide in the atmosphere is the increase in the amount of carbon dioxide emission from a factory, a power station, or a vehicle.

Therefore, in order to remove carbon dioxide in the atmosphere, researches on the electrochemical reduction of carbon dioxide and the production of useful synthetic gas based on the electrochemical reduction of carbon dioxide are ongoing.

However, the researches have been focused on a method for increasing production efficiency of synthetic gas, which can be obtained by reducing carbon dioxide, up to now, and researches on a more extensive system of utilizing carbon dioxide, which connects the produced synthetic gas with a subsequent process device, are insufficient.

SUMMARY

The present disclosure has been made in view of the above problems and it is an object of the present disclosure to provide a system of utilizing carbon dioxide, which effectively captures carbon dioxide to produce useful synthetic gas, conveniently stores and transfers the produced synthetic gas, and finally produces desired fuel gas and recycles the carbon dioxide by circulating the carbon dioxide.

In addition to the objects of the present disclosure as mentioned above, additional objects and features of the present disclosure will be clearly understood by those skilled in the art from the following description of the present disclosure.

In accordance with an aspect of the present disclosure, the above and other objects can be accomplished by the provision of a system of utilizing carbon dioxide, which comprises a carbon dioxide capturing device for capturing carbon dioxide, an electrochemical reaction device for producing synthetic gas by reducing the carbon dioxide captured by the carbon dioxide capturing device, a hydrogen carrier manufacturing device for manufacturing a hydrogen carrier material by using the synthetic gas produced by the electrochemical reaction device, a dehydrogenation device for producing hydrogen from the hydrogen carrier material manufactured by the hydrogen carrier manufacturing device, and a hydrogen utilization device for utilizing hydrogen produced by the dehydrogenation device, wherein the dehydrogenation device further produces carbon dioxide from the hydrogen carrier material and supplies the carbon dioxide to the carbon dioxide capturing device.

The carbon dioxide capturing device may include a tertiary aqueous amine solution containing $HCO_3^-$, and the tertiary aqueous amine solution containing $HCO_3^-$ may be supplied to the electrochemical reaction device.

The tertiary aqueous amine solution containing $HCO_3^-$ may be supplied to the electrochemical reaction device at a pressure of 5 bar or more.

The electrochemical reaction device may include a reduction electrode, an oxidation electrode, a separation membrane provided between the reduction electrode and the oxidation electrode, a reducing material circulator connected with the reduction electrode to give and take a tertiary aqueous amine solution, in which carbon dioxide is captured, to and from the reduction electrode, and an oxidizing material circulator connected with the oxidation electrode.

The reducing material circulator may supply the tertiary aqueous amine solution, in which carbon dioxide is captured, supplied from the carbon dioxide capturing device, to the reduction electrode, supply the synthetic gas produced from the reduction electrode to the hydrogen carrier manufacturing device, and supply an unreacted tertiary aqueous amine solution transferred from the reduction electrode to the reduction electrode.

The reduction electrode may produce the synthetic gas containing carbon monoxide and hydrogen from the tertiary aqueous amine solution, supply the synthetic gas to the reducing material circulator, and supply the unreacted tertiary aqueous amine solution to the reducing material circulator.

The reduction electrode may include a reduction catalyst electrode having a structure in which mixed particles of nanostructured silver (Ag) and carbon are stacked on a hydrophilic carbon support coated with silver (Ag).

The separation membrane may be formed of a bipolar membrane, and the bipolar membrane may be provided to allow $OH^-$ to move to the oxidation electrode, allow $H^+$ to move to the reduction electrode and allow $HCO_3^-$ not to move to the oxidation electrode.

The hydrogen carrier manufacturing device may include a multi-stage reactor for producing methanol by using carbon monoxide and hydrogen, which are produced as synthetic gas in the electrochemical reaction device, and a product collector for collecting a product from the multi-stage reactor, and the product collector may be connected with the dehydrogenation device without having a separate distiller at a rear end thereof.

The dehydrogenation device may include an oxidation electrode for producing carbon dioxide by reacting methanol manufactured in the hydrogen carrier manufacturing device with water, and a reduction electrode for producing hydrogen by receiving hydrogen ions from the oxidation electrode while facing the oxidation electrode with a separation membrane interposed therebetween, and the carbon dioxide produced from the oxidation electrode may be supplied to the carbon dioxide capturing device, and the hydrogen produced from the reduction electrode may be supplied to the hydrogen utilization device.

The hydrogen utilization device may be comprised of a hydrogen fuel cell.

In accordance with another aspect of the present disclosure, the above and other objects can be accomplished by the provision of a system of utilizing carbon dioxide, which comprises a carbon dioxide capturing device for capturing carbon dioxide, an electrochemical reaction device for producing synthetic gas by reducing the carbon dioxide captured by the carbon dioxide capturing device, an alcohol producing device for producing alcohol by using the synthetic gas produced in the electrochemical reaction device, and an alcohol reforming device for reforming the alcohol produced by the alcohol producing device, wherein the alcohol reforming device produces carbon dioxide from the alcohol and supplies the carbon dioxide to the carbon dioxide capturing device.

The carbon dioxide capturing device may include a tertiary aqueous amine solution containing $HCO_3^-$, and may capture the carbon dioxide in the form of $HCO_3^-$, the tertiary aqueous amine solution in which the carbon dioxide is captured in the form of $HCO_3^-$ may be supplied to the electrochemical reaction device.

The electrochemical reaction device may include a reduction electrode, an oxidation electrode, a separation membrane provided between the reduction electrode and the oxidation electrode, a reducing material circulator connected with the reduction electrode to give and take a tertiary aqueous amine solution, in which carbon dioxide is captured, to and from the reduction electrode, and an oxidizing material circulator connected with the oxidation electrode, and the reducing material circulator may supply the tertiary aqueous amine solution, in which carbon dioxide is captured, supplied from the carbon dioxide capturing device, to the reduction electrode, supply the synthetic gas produced from the reduction electrode to the alcohol producing device and supply an unreacted tertiary aqueous amine solution transferred from the reduction electrode to the reduction electrode, and the reduction electrode may produce the synthetic gas from the tertiary aqueous amine solution, supply the synthetic gas to the reducing material circulator and supply the unreacted tertiary aqueous amine solution to the reducing material circulator.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION

Figure 1:
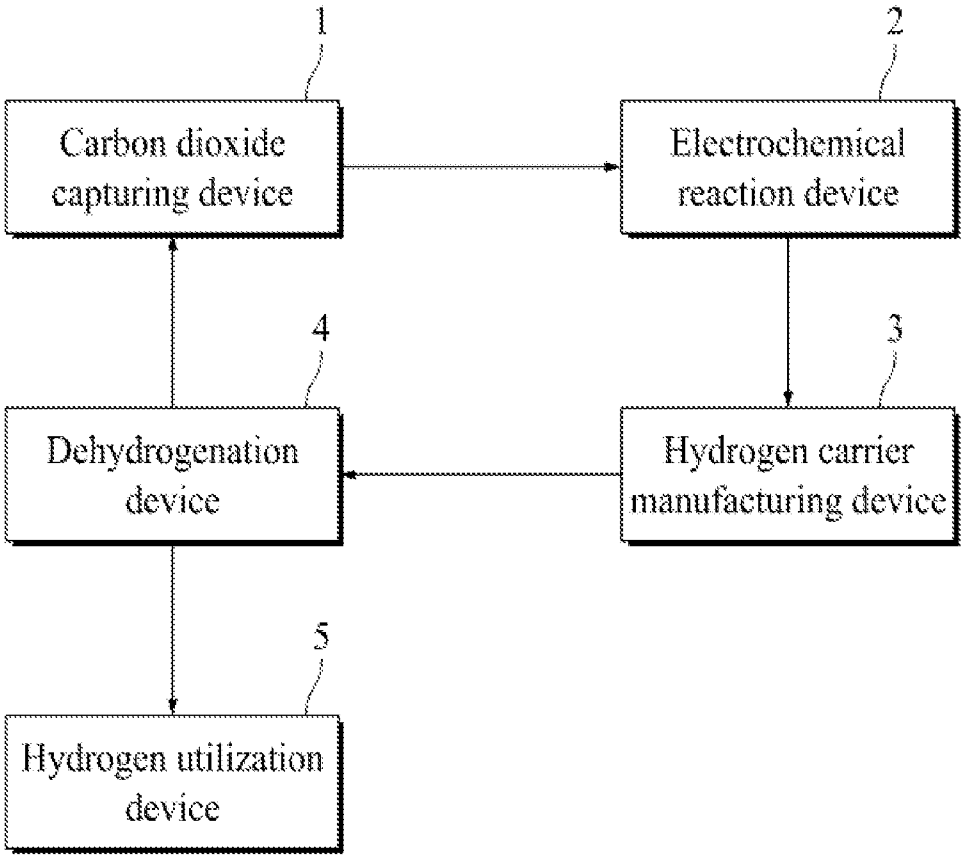
FIG. 1 is a schematic diagram illustrating a system of utilizing carbon dioxide in accordance with one embodiment of the present disclosure.

Advantages and features of the present disclosure and implementation methods thereof will be clarified through following embodiments described with reference to the accompanying drawings. The present disclosure may, however, be embodied in different forms and should not be construed as limited to the embodiments set forth herein. Rather, these embodiments are provided so that this disclosure will be thorough and complete and will fully convey the scope of the present disclosure to those skilled in the art. Further, the present disclosure is only defined by scopes of claims.

A shape, a size, a ratio, an angle and a number disclosed in the drawings for describing embodiments of the present disclosure are merely an example and thus, the present disclosure is not limited to the illustrated details. Like reference numerals refer to like elements throughout the specification. In the following description, when the detailed description of the relevant known function or configuration is determined to unnecessarily obscure the important point of the present disclosure, the detailed description will be omitted. In a case where 'comprise', 'have' and 'include' described in the present disclosure are used, another part may be added unless 'only~' is used. The terms of a singular form may include plural forms unless referred to the contrary.

In construing an element, the element is construed as including an error range although there is no explicit description.

In describing a position relationship, for example, when the position relationship is described as 'upon~', 'above~', 'below~' and 'next to~', one or more portions may be arranged between two other portions unless 'just' or 'direct' is used.

In describing a temporal relationship, for example, when the temporal order is described as 'after~', 'subsequent~', 'next~' and 'before~', a case which is not continuous may be included unless 'just' or 'direct' is used.

It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element, without departing from the scope of the present disclosure.

Features of various embodiments of the present disclosure may be partially or overall coupled to or combined with each other and may be variously inter-operated with each other and driven technically as those skilled in the art can sufficiently understand. The embodiments of the present disclosure may be carried out independently from each other or may be carried out together in co-dependent relationship.

Hereinafter, a preferred embodiment of the present disclosure will be described in detail with reference to the accompanying drawings.

FIG. 1 is a schematic diagram illustrating a system of utilizing carbon dioxide in accordance with one embodiment of the present disclosure.

As noted from FIG. 1, the system of utilizing carbon dioxide in accordance with one embodiment of the present disclosure includes a carbon dioxide capturing device 1, an electrochemical reaction device 2, a hydrogen carrier manufacturing device 3, a dehydrogenation device 4, and a hydrogen utilization device 5.

The carbon dioxide capturing device 1 is a device for capturing carbon dioxide produced in various fields, for example, carbon dioxide contained in the atmosphere and produced by a factory, a power station, a vehicle or the like, and includes an aqueous amine solution. In detail, the carbon dioxide capturing device 1 includes amine and water, wherein the amine includes a tertiary amine, preferably a tertiary amine having no OH group. The tertiary amine having no OH group may include triethylamine (TEA).

The triethylamine (TEA) may be expressed by $R_3N$ (where R is $CH_2CH_3$) such as the following chemical formula 1.

Chemical Formula 1

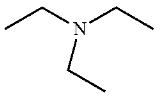

A carbon dioxide capturing reaction in the carbon dioxide capturing device 1 containing the aqueous amine solution is as expressed by the following reaction formula 1.

$$CO_2+R_3N+H_2O \rightarrow R_3NH^++HCO_3^-$$ Reaction Formula 1

Therefore, the carbon dioxide is contained in the aqueous amine solution in the state of ions such as $HCO_3^-$, and the aqueous amine solution containing such $HCO_3^-$ may be supplied to the electrochemical reaction device 2.

The electrochemical reaction device 2 produces synthetic gas by using the carbon dioxide captured in the carbon dioxide capturing device 1.

According to the related art, carbon dioxide is captured from emission gas and then separated and supplied to the electrochemical reaction device 2. However, according to one embodiment of the present disclosure, the carbon dioxide captured in the carbon dioxide capturing device 1 is supplied to the electrochemical reaction device 2 in the state of the carbon dioxide captured in the aqueous amine solution, more specifically the aqueous amine solution containing $HCO_3^-$ without a separation process for separating the carbon dioxide captured in the carbon dioxide capturing device 1 from the aqueous amine solution.

Therefore, the present disclosure has an advantage of saving the cost required for a carbon dioxide separation process as compared with the related art. In addition, in the related art, even though the carbon dioxide of high purity is separated through a separation process, carbon dioxide conversion efficiency is deteriorated due to a low production rate of synthetic gas produced from the electrochemical reaction device 2. On the other hand, in the present disclosure, since carbon dioxide of relatively low purity, which is not subjected to the separation process, is used, carbon dioxide conversion efficiency is more improved than that of the related art. Also, in the related art, a problem occurs in that the system is unstable due to crossover of the separated carbon dioxide into a counter electrode. However, in the present disclosure, since the carbon dioxide is supplied to the electrochemical reaction device 2 in the state that the carbon dioxide is captured in the aqueous amine solution, there is no crossover of the carbon dioxide into the counter electrode. In addition, although the related art requires an additional process of separating the synthetic gas produced in the electrochemical reaction device 2 from the carbon dioxide, the present disclosure does not require such additional process because the carbon dioxide circulates in the state that the carbon dioxide is captured in the aqueous amine solution.

The electrochemical reaction device 2 includes a reduction electrode, an oxidation electrode, and a separation membrane provided between the reduction electrode and the oxidation electrode, wherein carbon dioxide is reduced by the reduction electrode to produce synthetic gas of carbon monoxide (CO) and hydrogen ($H_2$). At this time, the carbon monoxide (CO) and the hydrogen ($H_2$) may be produced at a molar ratio of 1:2 to facilitate a manufacturing process of a hydrogen carrier in the hydrogen carrier manufacturing device 3.

Since the hydrogen ($H_2$) produced in the electrochemical reaction device 2 is not easy to carry in the state of gas, it is manufactured by the hydrogen carrier manufacturing device 3 as a hydrogen carrier of a liquid state, which is easy to carry.

The hydrogen carrier manufacturing device 3 may produce methanol as a hydrogen carrier by using the synthetic gas of carbon monoxide (CO) and hydrogen ($H_2$), which are produced in the electrochemical reaction device 2.

The hydrogen carrier manufacturing device 3 may produce 1 mole of methanol ($CH_3OH$) by reacting 1 mole of carbon monoxide (CO) with 2 moles of hydrogen ($H_2$) using a thermochemical reactor. This reaction may be performed by an exothermic reaction, and may improve a methanol production rate by using a multi-stage reactor.

The dehydrogenation device 4 may produce hydrogen ($H_2$) by reforming the methanol manufactured by the hydrogen carrier manufacturing device 3. In detail, the dehydrogenation device 4 may produce carbon dioxide and hydrogen by reacting the methanol with water. The dehydrogenation device 4 may include an electrochemical reactor that includes an oxidation electrode, a reduction electrode, and a separation membrane provided between the oxidation electrode and the reduction electrode. The carbon dioxide may be produced from the oxidation electrode of the electrochemical reactor, and the hydrogen may be produced from the reduction electrode of the electrochemical reactor.

The carbon dioxide produced by the dehydrogenation device 4 is supplied to the carbon dioxide capturing device 1 and then circulates therein, and the hydrogen produced by the dehydrogenation device 4 is supplied to the hydrogen utilization device 5. Therefore, the system according to one embodiment of the present disclosure may obtain hydrogen which is a useful material that may be used for various purposes in accordance with circulation of carbon dioxide.

The hydrogen utilization device 5 may be any of a variety of devices known in the art that can utilize hydrogen. For example, the hydrogen utilization device 5 may include a hydrogen fuel cell that uses hydrogen as fuel.

Figure 2:
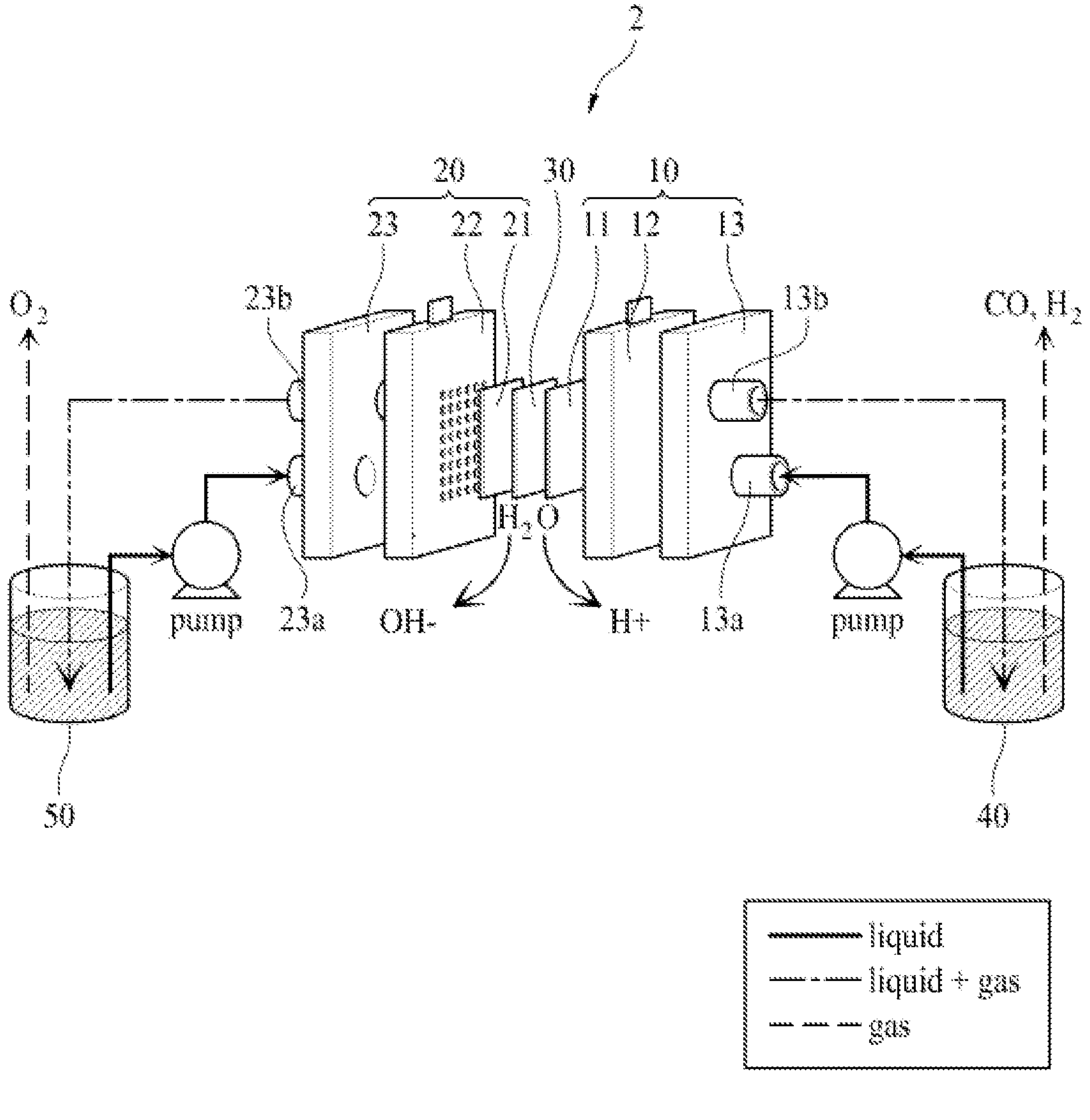
FIG. 2 is a schematic diagram illustrating an electrochemical reaction device applied to a system utilizing carbon dioxide in accordance with one embodiment of the present disclosure.

FIG. 2 is a schematic diagram illustrating an electrochemical reaction device 2 applied to the system of utilizing carbon dioxide in accordance with one embodiment of the present disclosure.

As noted from FIG. 2, the electrochemical reaction device 2 according to one embodiment of the present disclosure includes a reduction electrode 10, an oxidation electrode 20, a separation membrane 30, a reducing material circulator 40, and an oxidizing material circulator 50.

The reduction electrode 10 is an electrode in which carbon dioxide is reduced to produce carbon monoxide and hydrogen, and includes a first catalyst unit 11, a first flow path unit 12, and a first entrance/exit unit 13.

The first catalyst unit 11 may include a reduction catalyst electrode. The reduction catalyst electrode may have a structure in which mixed particles of nanostructured silver (Ag) and carbon are stacked on a hydrophilic carbon support coated with silver (Ag). Silver (Ag) is known as a catalyst for reducing carbon dioxide, and when mixed particles of nanostructured silver (Ag) and carbon are stacked on the hydrophilic carbon support coated with silver (Ag) and then used as a reduction catalyst electrode, a synthetic gas production rate of carbon monoxide and hydrogen is excellent.

A manufacturing process of the reduction catalyst electrode according to one embodiment of the present disclosure is as follows.

First of all, silver (Ag) is coated on a hydrophilic carbon support by an e-beam process without hydrophobic treatment on the hydrophilic carbon support. According to one embodiment of the present disclosure, since the aqueous amine solution in which carbon dioxide is captured is supplied to the reduction electrode 10, the carbon support has a hydrophilic property. In addition, conductivity of the reduction catalyst electrode may be improved by the silver (Ag) coating, whereby a production rate of the synthetic gas may be improved.

Next, mixed particles of silver (Ag) and carbon black are coated on the hydrophilic carbon support coated with silver (Ag). In this way, according to one embodiment of the present disclosure, silver (Ag) particles are not used alone but mixed particles of silver (Ag) and carbon are used, whereby conductivity and mass diffusion may be enhanced. Carbon nanotube and the like in addition to carbon black may be used as the carbon.

Next, mixed particles of nanostructured silver (Ag) and carbon are formed through an electrochemical process of two steps. In detail, in the first step, silver chloride is formed through an electrochemical oxidation process. In the second step, an oxidized silver chloride is reduced again to obtain nanostructured silver (Ag). In this way, the nanostructured silver (Ag) may be used as a material of the reduction catalyst electrode, whereby conversion efficiency of carbon dioxide may be improved. Also, since the hydrophilic property of the carbon particles may be enhanced through such a nanostructured process, conversion efficiency of carbon dioxide may be improved when the aqueous amine solution in which carbon dioxide is captured is supplied to the reduction electrode 10.

Figure 3:
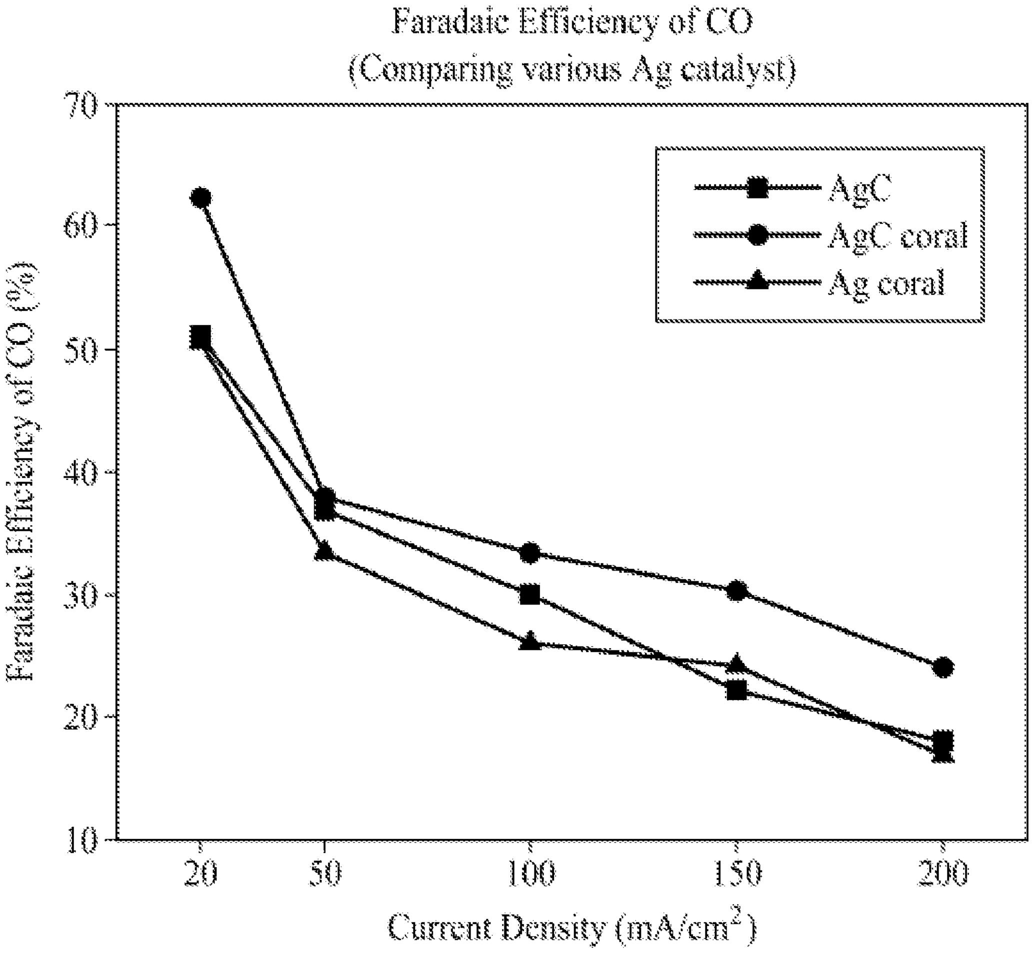
FIG. 3 is a graph illustrating Faraday efficiency of carbon monoxide with respect to a current density of a reduction catalyst electrode according to various embodiments of the present disclosure.

FIG. 3 is a graph illustrating Faraday efficiency of carbon monoxide with respect to a current density of a reduction catalyst electrode according to various embodiments of the present disclosure.

In FIG. 3, AgC is an embodiment in which a process of forming mixed particles of nanostructured silver and carbon through the electrochemical process, which is the second step in the aforementioned manufacturing process of the reduction catalyst electrode, is not performed. AgC coral is an embodiment in which the manufacturing process of the reduction catalyst electrode is performed. Ag coral is an embodiment in which mixed particles of silver and carbon black are not coated on the hydrophilic carbon support coated with silver but Ag excluding carbon black is only coated thereon in the aforementioned manufacturing process of the reduction catalyst electrode.

As noted from FIG. 3, it is noted that production efficiency of carbon monoxide through reduction of carbon dioxide is the most excellent in case of AgC coral that is the embodiment in which the manufacturing process of the reduction catalyst electrode is performed at various current densities.

Referring back to FIG. 2, the first flow path unit 12 facilitates a carbon dioxide reduction reaction by allowing the aqueous amine solution, in which carbon dioxide supplied through the first entrance/exist unit 13 is captured, to be easily in contact with the first catalyst unit 11. Therefore, the first flow path unit 12 is provided with a flow path of the aqueous amine solution, in which carbon dioxide is captured, on a surface facing the first catalyst unit 11. The first flow path unit 12 may serve as a current collector of the reduction electrode 10.

The first entrance/exit unit 13 connects the reducing material circulator 40 with the first flow path unit 12, and includes a first inlet 13*a* and a first outlet 13*b*.

The aqueous amine solution having captured carbon dioxide which is stored in the reducing material circulator 40 enters the reduction electrode 10 through the first inlet 13*a*, and synthetic gas produced through reduction of carbon dioxide near the first catalyst unit 11 and an aqueous amine solution having captured carbon dioxide which is unreacted are discharged from the first outlet 13*b* to the outside of the reduction electrode 10. The synthetic gas and the aqueous amine solution having captured carbon dioxide which is unreacted, which are discharged from the first outlet 13*b*, are again supplied to the reducing material circulator 40. At this time, the synthetic gas containing carbon monoxide and hydrogen is separated from the reducing material circulator 40 and then supplied to the hydrogen carrier manufacturing device 3, and the aqueous amine solution having captured carbon dioxide which is unreacted moves into the reduction electrode 10 through the first inlet 13*a*.

The reduction electrode 10 described as above produces carbon monoxide while generating a continuous reaction of the following reaction formulas 2 and 3.

$$HCO_3^- + H^+ \rightarrow CO_2 + H_2O \quad \text{Reaction formula 2}$$

$$CO_2 + H_2O + 2e^- \rightarrow CO + 2OH^- \quad \text{Reaction formula 3}$$

The oxidation electrode 20 is an electrode in which water is decomposed to produce oxygen, and includes a second catalyst unit 21, a second flow path unit 22, and a second entrance/exit unit 23.

The second catalyst unit 21 may include an oxidation catalyst electrode. The oxidation catalyst electrode may include a nickel electrode, but is not limited thereto. Various electrode materials known in the art may be used as the oxidation catalyst electrode.

The second flow path unit 22 facilitates an oxidation reaction by allowing an electrolyte solution supplied through the second entrance/exit unit 23 to be easily in contact with the second catalyst unit 21. Therefore, the second flow path unit 22 is provided with a flow path of the electrolyte solution on a surface facing the second catalyst unit 21. The second flow path unit 22 may serve as a current collector of the oxidation electrode 20.

The second entrance/exit unit 23 connects the oxidizing material circulator 50 with the second flow path unit 22, and includes a second inlet 23*a* and a second outlet 23*b*.

The electrolyte solution stored in the oxidizing material circulator 50 is supplied to the oxidation electrode 20 through the second inlet 23*a*, and oxygen, which is produced in the vicinity of the second catalyst unit 21, and the electrolyte solution are discharged through the second outlet 23*b* to the outside of the oxidation electrode 20. The electrolyte solution discharged from the second outlet 23*b* is again supplied to the oxidizing material circulator 50. At this time, oxygen may be separated from the oxidizing material circulator 50.

The oxidation electrode 10 described as above produces oxygen while generating a reaction of the following reaction formula 4.

$$2OH^- \rightarrow 2e^- + 1/2O_2 + H_2O \quad \text{Reaction formula 4}$$

The separation membrane 30 is disposed between the reduction electrode 10 and the oxidation electrode 20. The separation membrane 30 is preferably formed of a bipolar membrane.

When the separation membrane 30 is made of an anion exchange membrane, bicarbonate ions (HCO3—) contained in a tertiary aqueous amine solution may move toward the oxidation electrode 20. As a result, the amount of carbon dioxide existing in the reduction electrode 10 is reduced, whereby efficiency of the synthetic gas production reaction performed in the reduction electrode 10 may be deteriorated.

Also, when the separation membrane 30 is formed of a cation exchange membrane, a hydrogenated amine, such as $(CH_2CH_3)_3NH^+$ ion, which is contained in the tertiary aqueous amine solution, may move toward the oxidation electrode 20, and an electrolyte cation in the aqueous solution of the oxidation electrode 20, for example, potassium ions ($K^+$) derived from potassium hydroxide may move toward the reduction electrode 10. As a result, efficiency of the synthetic gas production reaction performed in the reduction electrode 10 may be deteriorated.

In contrast, when the separation membrane 30 is formed of a bipolar membrane, the separation membrane 30 allows $OH^-$ to move to the oxidation electrode 20, and allows $H^+$ to move to the reduction electrode 10. Also, the separation membrane 30 allows $HCO_3^-$ not to move to the oxidation electrode 20, whereby hydrogen production efficiency may be improved in the reduction electrode 10, and oxygen production efficiency may be improved in the oxidation electrode 20.

The reducing material circulator 40 supplies the aqueous amine solution, in which carbon dioxide is captured, to the reduction electrode 10, and serves to accommodate the synthetic gas produced by the reduction electrode 10 and the aqueous amine solution having captured carbon dioxide which is unreacted.

A pump may be provided between the reducing material circulator 40 and the reduction electrode 10 to supply the aqueous amine solution, in which carbon dioxide is captured, to the reduction electrode 10 in a state of 5 bar or more, preferably in a high pressure state of 20 bar or more.

Figure 4:
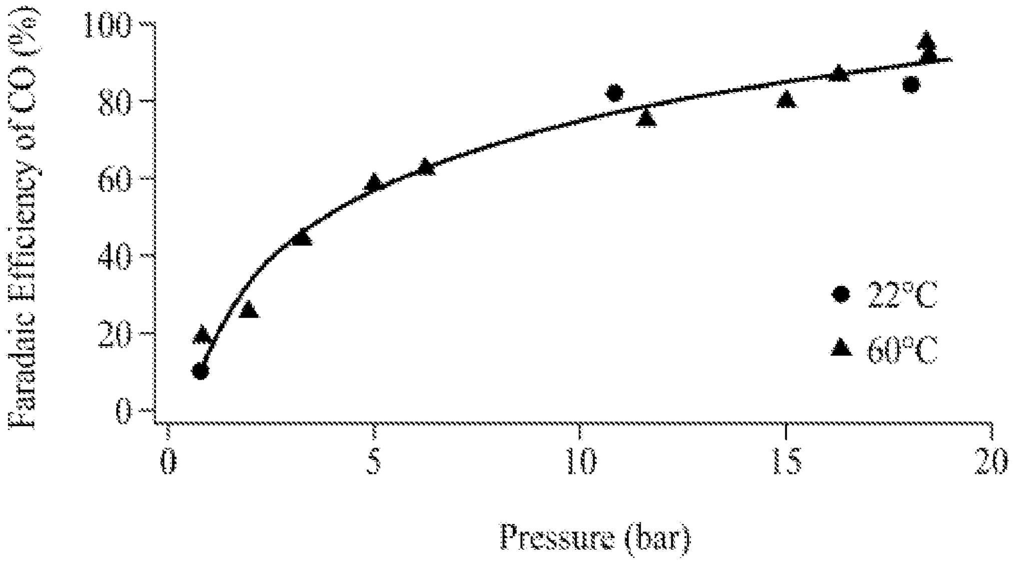
FIG. 4 is a graph illustrating Faraday efficiency of carbon monoxide with respect to a pressure of a tertiary aqueous amine solution supplied to an electrochemical reaction device.

FIG. 4 is a graph illustrating Faraday efficiency of carbon monoxide with respect to a pressure of a tertiary aqueous amine solution supplied to an electrochemical reaction device.

Faraday efficiency measured at 22° C. and Faraday efficiency measured at 60° C. are shown in FIG. 4. As noted from FIG. 4, it is noted that Faraday efficiency of the carbon monoxide is increased as the pressure of the tertiary aqueous amine solution supplied to the electrochemical reaction device is increased. Therefore, according to one embodiment of the present disclosure, it is noted that production efficiency of the carbon monoxide is improved as the pressure of the tertiary aqueous amine solution supplied to the electrochemical reaction device is increased.

According to one embodiment of the present disclosure, the tertiary aqueous amine solution may be supplied to the electrochemical reaction device 2 at a pressure of 5 bar or more, and the tertiary aqueous amine solution may maintain a pressure of 5 bar or more in the electrochemical reaction device 2. Preferably, the tertiary aqueous amine solution may be supplied to the electrochemical reaction device 2 at a pressure of 20 bar or more, and the tertiary aqueous amine solution may maintain a pressure of 20 bar or more in the electrochemical reaction device 2.

According to one embodiment of the present disclosure, it may be preferable that the pressure of the tertiary aqueous amine solution in the electrochemical reaction device 2 ranges from 5 bar to 50 bar. This is because that production efficiency of carbon monoxide (CO) may be deteriorated when the pressure of the tertiary aqueous amine solution in the electrochemical reaction device 2 is less than 5 bar and production efficiency of carbon monoxide (CO) may be not improved additionally even though the pressure of the tertiary aqueous amine solution exceeds 50 bar in the electrochemical reaction device 2.

Referring back to FIG. 2, the synthetic gas is separated from the reducing material circulator 40 and supplied to the aforementioned hydrogen carrier manufacturing device 3, and the aqueous amine solution having captured carbon dioxide which is unreacted circulates while moving into the reduction electrode 10.

The oxidizing material circulator 50 supplies an electrolyte aqueous solution, such as KOH, to the oxidation electrode 20, and serves to accommodate oxygen produced from the oxidation electrode 20 and the electrolyte aqueous solution.

A pump may also be provided between the oxidizing material circulator 50 and the oxidation electrode 20.

As described above, the oxygen is separated from the oxidizing material circulator 50, and the electrolyte aqueous solution circulates while moving into the oxidation electrode 20.

Figure 5:
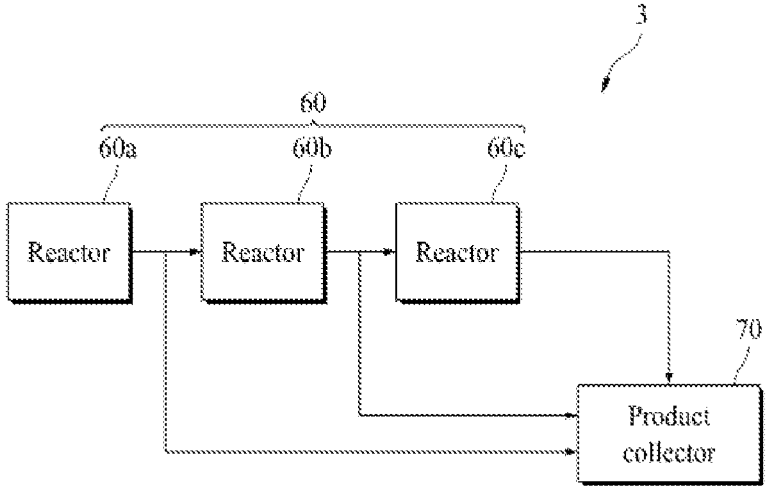
FIG. 5 is a schematic diagram illustrating a hydrogen carrier manufacturing device applied to a system of utilizing carbon dioxide in accordance with one embodiment of the present disclosure.

FIG. 5 is a schematic diagram illustrating a hydrogen carrier manufacturing device 3 applied to a system of utilizing carbon dioxide in accordance with one embodiment of the present disclosure.

As noted from FIG. 5, the hydrogen carrier manufacturing device 3 according to one embodiment of the present disclosure includes a multi-stage reactor 60 and a product collector 70.

The multi-stage reactor 60 includes a plurality of reactors 60*a*, 60*b* and 60*c* for producing methanol using carbon monoxide and hydrogen.

The plurality of reactors 60*a*, 60*b* and 60*c* include a first reactor 60*a*, a second reactor 60*b* and a third reactor 60*c*, which are connected to one another in series and arranged in due order. Although three reactors 60*a*, 60*b* and 60*c* are shown in the drawing, the number of the reactors may be changed diversely.

The first reactor 60*a* is supplied with carbon monoxide and hydrogen, which are produced from the aforementioned electrochemical reaction device 2, produces 1 mole of methanol by reacting 1 mole of carbon monoxide with 2 moles of hydrogen, supplies the produced methanol to the product collector 70, and supplies unreacted carbon monoxide and hydrogen to the second reactor 60*b*.

The second reactor 60*b* produces methanol by reacting carbon monoxide and hydrogen, which are supplied from the first reactor 60*a*, with each other, supplies the produced methanol to the product collector 70, and supplies unreacted carbon monoxide and hydrogen to the third reactor 60*c*.

The third reactor 60*c* produces methanol by reacting carbon monoxide and hydrogen, which are supplied from the second reactor 60*b*, with each other, and supplies the produced methanol to the product collector 70.

The product collector 70 collects the methanol produced in the individual reactors 60*a*, 60*b* and 60*c*.

According to one embodiment of the present disclosure, carbon monoxide and hydrogen, which are produced in the aforementioned electrochemical reaction device 2, are supplied to the first reactor 60*a*, and carbon dioxide is not supplied to the first reactor 60*a*. Therefore, in the plurality of reactors 60*a*, 60*b* and 60*c*, methanol is produced and water is not produced as a by-product. As a result, a separate separator, such as a distiller for separating water that is a by-product, is not required at a rear end of the product collector 70.

When carbon dioxide is supplied into the individual reactors 60*a*, 60*b* and 60*c* together with carbon monoxide and hydrogen, water as well as methanol may be produced as a product, and thus a separate distiller for separating water from methanol is required at the rear end of the product collector 70.

However, according to one embodiment of the present disclosure, since carbon monoxide and hydrogen, which are produced in the electrochemical reaction device 2, are supplied to the first reactor 60*a* of the hydrogen carrier manufacturing device 3 but carbon dioxide is not supplied to the first reactor 60*a*, a separate separator, such as a distiller, is not required at the rear end of the product collector 70.

Therefore, the product collector 70 of the hydrogen carrier manufacturing device 3 may be directly connected with the dehydrogenation device 4 without a separate separator, such as a distiller, at the rear end thereof.

Figure 6:
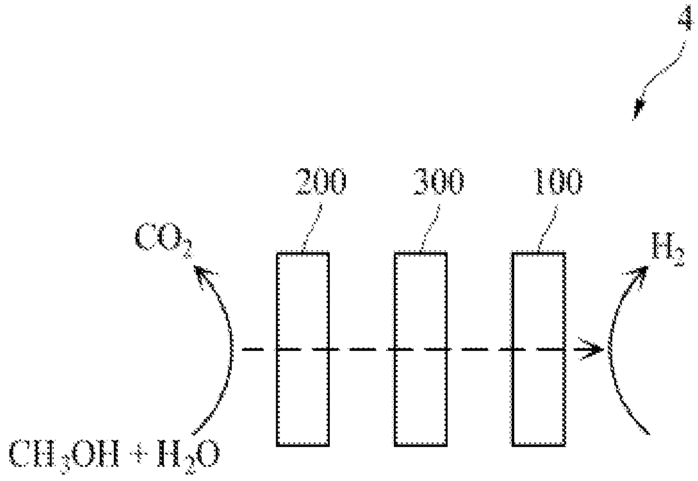
FIG. 6 is a schematic diagram illustrating a dehydrogenation device applied to a system of utilizing carbon dioxide in accordance with one embodiment of the present disclosure.

FIG. 6 is a schematic diagram illustrating a dehydrogenation device 4 applied to a system of utilizing carbon dioxide in accordance with one embodiment of the present disclosure.

As shown in FIG. 6, the dehydrogenation device 4 according to one embodiment of the present disclosure includes a reduction electrode 100, an oxidation electrode 200, and a separation membrane 300.

Although not shown in detail, the reduction electrode 100 may include a first catalyst unit, a first flow path unit, and a first entrance/exit unit, similarly to the reduction electrode 10 of FIG. 2. However, a reduction catalyst electrode and an entrance/exit material of the reduction electrode 100 are different from those of the reduction electrode 10 of FIG. 2.

Although not shown in detail, the oxidation electrode 200 may include a second catalyst unit, a second flow path unit, and a second entrance/exit unit, similarly to the oxidation electrode 20 of FIG. 2. However, an oxidation catalyst electrode and an entrance/exit material of the oxidation electrode 200 are different from those of the oxidation electrode 10 of FIG. 2.

The oxidation electrode 200 is supplied with water and methanol, which is manufactured by the hydrogen carrier manufacturing device 3, to produce carbon dioxide, and the produced carbon dioxide is supplied to the aforementioned carbon dioxide capturing device 1.

Hydrogen ions ($H^+$) produced by the oxidation electrode 200 pass through the separation membrane 300 and then are supplied with electrons $e^-$ from the reduction electrode 100 to produce hydrogen, and the produced hydrogen is supplied to the hydrogen utilization device 5.

The separation membrane 300 may be provided between the reduction electrode 100 and the oxidation electrode 200, and may be formed of a conductive film to allow the hydrogen ions $H^+$ produced from the oxidation electrode 200 to move to the reduction electrode 100.

In the dehydrogenation device 4 described as above, hydrogen and carbon dioxide are produced by a reaction based on the following reaction formula 5.

$$CH_3OH+H_2O\rightarrow 3H_2+CO_2$$ Reaction formula 5

Figure 7:
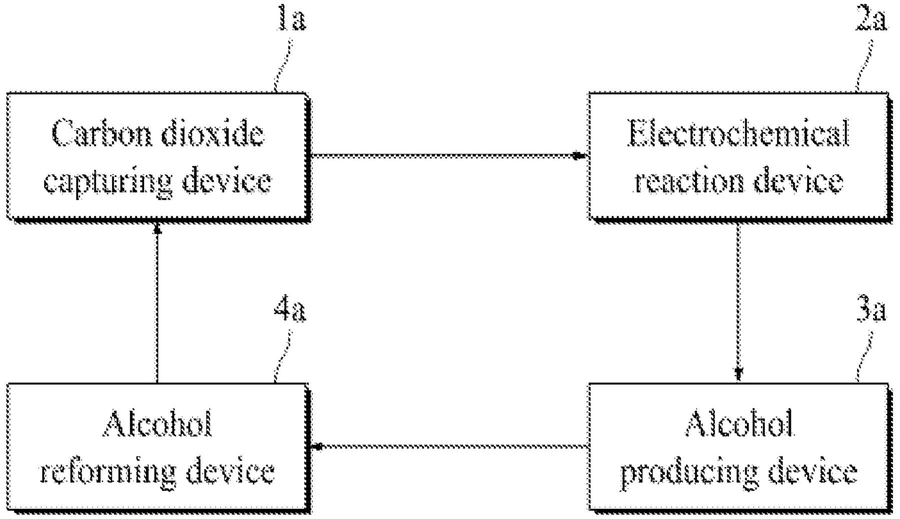
FIG. 7 is a schematic diagram illustrating a system of utilizing carbon dioxide in accordance with another embodiment of the present disclosure.

FIG. 7 is a schematic diagram illustrating a system of utilizing carbon dioxide in accordance with another embodiment of the present disclosure.

As noted from FIG. 7, the system of utilizing carbon dioxide in accordance with another embodiment of the present disclosure includes a carbon dioxide capturing device 1*a*, an electrochemical reaction device 2*a*, an alcohol producing device 3*a*, and an alcohol reforming device 4*a*.

Since the carbon dioxide capturing device 1*a* is the same as the carbon dioxide capturing device 1 of FIG. 1, its repeated description will be omitted.

The electrochemical reaction device 2*a* may be configured to be the same as the electrochemical reaction device 2 of FIG. 1, and may be provided to produce synthetic gas of carbon monoxide and hydrogen. However, the electrochemical reaction device 2*a* according to FIG. 7 may be provided to produce another type of synthetic gas unlike the electrochemical reaction device 2 of FIG. 1.

The alcohol producing device 3*a* may be configured to be the same as the hydrogen carrier manufacturing device 3 of FIG. 1 to produce methanol. However, unlike the hydrogen carrier manufacturing device 3 of FIG. 1, the alcohol producing device 3*a* according to FIG. 7 may be configured to produce another type of alcohol, for example, ethanol or butanol.

The alcohol reforming device 4*a* may be configured to be the same as the dehydrogenation device 4 of FIG. 1 to produce carbon dioxide and hydrogen. However, unlike the dehydrogenation device 4 of FIG. 1, the alcohol reforming device 4*a* according to FIG. 7 may be configured to produce carbon dioxide and another fuel gas. At this time, the carbon dioxide produced in the alcohol reforming device 4*a* is supplied to the carbon dioxide capturing device 1*a* and circulates. In addition, the fuel gas produced by the alcohol reforming device 4*a* may be supplied to various fuel devices, and when hydrogen is produced in the alcohol reforming device 4*a* as shown in FIG. 1, the hydrogen may be supplied to the hydrogen utilization device 5 of FIG. 1.

According to the present disclosure described above, the following advantageous effects may be obtained.

According to one embodiment of the present disclosure, the aqueous amine solution in which carbon dioxide is captured, more specifically the aqueous amine solution containing $HCO_3^-$ is supplied to the electrochemical reaction device without a separation process for separating the captured carbon dioxide from the aqueous amine solution. Therefore, the cost for the carbon dioxide separation process is saved, carbon dioxide conversion efficiency is improved, and crossover the carbon dioxide into the counter electrode does not occur.

According to one embodiment of the present disclosure, since the aqueous amine solution in which carbon dioxide is captured, more specifically the aqueous amine solution containing $HCO_3^-$ is supplied to the electrochemical reaction device and then circulates between the reduction electrode and the reducing material circulator, additional process of separating the produced synthetic gas from the carbon dioxide is not required.

According to one embodiment of the present disclosure, the reduction electrode of the electrochemical reaction device includes a reduction catalyst electrode having a structure in which mixed particles of nanostructured silver (Ag) and carbon are stacked on the hydrophilic carbon support coated with silver (Ag), whereby an excellent synthetic gas production rate of carbon monoxide and hydrogen is obtained.

According to one embodiment of the present disclosure, as the separation membrane of the electrochemical reaction device is formed of a bipolar membrane, hydrogen production efficiency in the reduction electrode may be improved, and oxygen production efficiency in the oxidation electrode may be improved.

According to one embodiment of the present disclosure, since carbon monoxide and hydrogen, which are produced in the electrochemical reaction device, are supplied to the reactor of the hydrogen carrier manufacturing device and carbon dioxide is not supplied to the reactor, methanol is produced in the reactor and water is not produced as a by-product, whereby a separate distiller for separating water that is a by-product is not required.

According to one embodiment of the present disclosure, the dehydrogenation device produces hydrogen and supplies the produced hydrogen to the hydrogen utilization device, and also produces carbon dioxide and supplies the produced carbon dioxide to the carbon dioxide capturing device, whereby the carbon dioxide may be recycled by circulation.

It will be apparent to those skilled in the art that the present disclosure described above is not limited by the above-described embodiments and the accompanying drawings and that various substitutions, modifications and variations may be made in the present disclosure without departing from the spirit or scope of the disclosures. Consequently, the scope of the present disclosure is defined by the accompanying claims and it is intended that all variations or modifications derived from the meaning, scope and equivalent concept of the claims fall within the scope of the present disclosure.

What is claimed is:

1. A system of utilizing carbon dioxide, the system comprising:

a carbon dioxide capturing device for capturing carbon dioxide;

an electrochemical reaction device for producing synthetic gas by reducing the carbon dioxide captured by the carbon dioxide capturing device;

a hydrogen carrier manufacturing device for manufacturing a hydrogen carrier material by using the synthetic gas produced by the electrochemical reaction device;

a dehydrogenation device for producing hydrogen from the hydrogen carrier material manufactured by the hydrogen carrier manufacturing device; and a hydrogen utilization device for utilizing hydrogen produced by the dehydrogenation device, wherein the hydrogen carrier manufacturing device includes a multi-stage reactor for producing methanol by using carbon monoxide and hydrogen, which are produced as the synthetic gas in the electrochemical reaction device, and a product collector for collecting the methanol from the multi-stage reactor, and the product collector is connected with the dehydrogenation device to supply the methanol to the dehydrogenation device, wherein the dehydrogenation device further produces carbon dioxide from the methanol of the hydrogen carrier material and supplies the produced carbon dioxide to the carbon dioxide capturing device to recycle the carbon dioxide by circulating the carbon dioxide, wherein carbon dioxide is not supplied to the multi-stage reactor so that water is not produced as a product for the hydrogen carrier manufacturing device, wherein the product collector of the hydrogen carrier manufacturing device is directly connected with the dehydrogenation device without a separate separator, wherein the electrochemical reaction device includes a reduction electrode, an oxidation electrode, a separation membrane provided between the reduction electrode and the oxidation electrode, wherein the reduction electrode takes a tertiary aqueous amine solution, in which carbon dioxide is captured, and wherein the reduction electrode includes a reduction catalyst electrode having a structure in which mixed particles of nanostructured silver (Ag) and carbon are stacked on a hydrophilic carbon support coated with silver (Ag).

2. The system of claim 1, wherein the carbon dioxide capturing device includes a tertiary aqueous amine solution containing $HCO_3^-$, and the tertiary aqueous amine solution containing $HCO_3^{31}$ is supplied to the electrochemical reaction device.

3. The system of claim 2, wherein the tertiary aqueous amine solution containing $HCO_3^-$ is supplied to the electrochemical reaction device at a pressure of 5 bar or more.

4. The system of claim 1, wherein the electrochemical reaction device further includes a reducing material circulator connected with the reduction electrode to give and take the tertiary aqueous amine solution, in which carbon dioxide is captured, to and from the reduction electrode, and an oxidizing material circulator connected with the oxidation electrode.

5. The system of claim 4, wherein the reducing material circulator supplies the tertiary aqueous amine solution, in which carbon dioxide is captured, supplied from the carbon dioxide capturing device, to the reduction electrode, supplies the synthetic gas produced in the reduction electrode to the hydrogen carrier manufacturing device, and supplies an unreacted tertiary aqueous amine solution transferred from the reduction electrode to the reduction electrode, and the reduction electrode produces the synthetic gas containing carbon monoxide and hydrogen from the tertiary aqueous amine solution, supplies the synthetic gas to the reducing material circulator, and supplies the unreacted tertiary aqueous amine solution to the reducing material circulator.

6. The system of claim 4, wherein the separation membrane is formed of a bipolar membrane, and the bipolar membrane is provided to allow $OH^-$ to move to the oxidation electrode, allow $H^+$ to move to the reduction electrode and allow $HCO_3^-$ not to move to the oxidation electrode.

7. The system of claim 1, wherein the dehydrogenation device includes an oxidation electrode for producing carbon dioxide by reacting methanol manufactured in the hydrogen carrier manufacturing device with water, and a reduction electrode for producing hydrogen by receiving hydrogen ions from the oxidation electrode while facing the oxidation electrode with a separation membrane interposed therebetween, the carbon dioxide produced from the oxidation electrode is supplied to the carbon dioxide capturing device, and the hydrogen produced from the reduction electrode is supplied to the hydrogen utilization device.

8. The system of claim 1, wherein the hydrogen utilization device is comprised of a hydrogen fuel cell.

9. A system of utilizing carbon dioxide, the system comprising:

a carbon dioxide capturing device for capturing carbon dioxide;

an electrochemical reaction device for producing synthetic gas by reducing the carbon dioxide captured by the carbon dioxide capturing device;

an alcohol producing device for producing alcohol by using the synthetic gas produced in the electrochemical reaction device; and an alcohol reforming device for reforming the alcohol produced by the alcohol producing device, wherein the alcohol producing device includes a multi-stage reactor for producing methanol by using carbon monoxide and hydrogen, which are produced as the synthetic gas in the electrochemical reaction device, and a product collector for collecting the methanol from the multi-stage reactor, and the product collector is connected with the alcohol reforming device to supply the methanol to the alcohol reforming device, wherein the alcohol reforming device produces carbon dioxide from the methanol and supplies the carbon dioxide to the carbon dioxide capturing device to recycle the carbon dioxide by circulating the carbon dioxide, wherein carbon dioxide is not supplied to the multi-stage reactor so that water is not produced as a product for the alcohol producing device, wherein the product collector of the alcohol producing device is directly connected with the alcohol reforming device without a separate separator, wherein the electrochemical reaction device includes a reduction electrode, an oxidation electrode, a separation membrane provided between the reduction electrode and the oxidation electrode, wherein the reduction electrode takes a tertiary aqueous amine solution, in which carbon dioxide is captured, and wherein the reduction electrode includes a reduction catalyst electrode having a structure in which mixed particles of nanostructured silver (Ag) and carbon are stacked on a hydrophilic carbon support coated with silver (Ag).

10. The system of claim 9, wherein the carbon dioxide capturing device includes the tertiary aqueous amine solution containing $HCO_3^-$, and the tertiary aqueous amine solution containing $HCO_3^-$ is supplied to the electrochemical reaction device.

11. The system of claim 9, wherein the electrochemical reaction device further includes a reducing material circulator connected with the reduction electrode to give and take the tertiary aqueous amine solution, in which carbon dioxide is captured, to and from the reduction electrode, and an oxidizing material circulator connected with the oxidation electrode, and the reducing material circulator supplies the tertiary aqueous amine solution, in which carbon dioxide is captured, supplied from the carbon dioxide capturing device, to the reduction electrode, supplies the synthetic gas produced in the reduction electrode to the alcohol producing device and supplies an unreacted tertiary aqueous amine solution transferred from the reduction electrode to the reduction electrode, and the reduction electrode produces the synthetic gas from the tertiary aqueous amine solution, supplies the synthetic gas to the reducing material circulator, and supplies the unreacted tertiary aqueous amine solution to the reducing material circulator.

* * * * *